United States Patent
Yahagi et al.

(10) Patent No.: US 12,082,779 B2
(45) Date of Patent: Sep. 10, 2024

(54) ENDOSCOPE HOLDER

(71) Applicants: KEIO UNIVERSITY, Tokyo (JP); WAKO INDUSTRIES CO., LTD., Saitama (JP); SAITAMA CHAMBER OF COMMERCE AND INDUSTRY, Saitama (JP)

(72) Inventors: Naohisa Yahagi, Tokyo (JP); Norihito Wada, Tokyo (JP); Itsuro Ogawa, Saitama (JP); Satoru Ogawa, Saitama (JP); Yuzuru Inoue, Tokyo (JP); Mitsuru Yoda, Tokyo (JP)

(73) Assignees: KEIO UNIVERSITY, Tokyo (JP); WAKO INDUSTRIES CO., LTD., Saitama (JP); SAITAMA CHAMBER OF COMMERCE AND INDUSTRY, Saitama (JP)

( * ) Notice: Subject to any disclaimer, the term of this patent is extended or adjusted under 35 U.S.C. 154(b) by 0 days.

(21) Appl. No.: 17/943,305

(22) Filed: Sep. 13, 2022

(65) Prior Publication Data
US 2023/0000323 A1    Jan. 5, 2023

Related U.S. Application Data

(62) Division of application No. 16/089,629, filed as application No. PCT/JP2017/006160 on Feb. 20, 2017, now Pat. No. 11,464,396.

(30) Foreign Application Priority Data

Mar. 31, 2016  (JP) .................................. 2016-069938
Dec. 26, 2016  (JP) .................................. 2016-251858
Jan. 30, 2017  (JP) .................................. 2017-014787

(51) Int. Cl.
*A61B 1/00*    (2006.01)
*A61B 1/01*    (2006.01)

(52) U.S. Cl.
CPC ...... *A61B 1/00147* (2013.01); *A61B 1/00071* (2013.01); *A61B 1/0014* (2013.01); *A61B 1/00149* (2013.01); *A61B 1/01* (2013.01)

(58) Field of Classification Search
CPC ............ A61B 1/00101; A61B 1/00089; A61B 1/00131; A61B 1/00133; A61B 1/0014; (Continued)

(56) References Cited

U.S. PATENT DOCUMENTS 6,358,199 B1 *  3/2002  Pauker ............... A61B 1/00133
                                                      600/102
6,554,766 B2 *  4/2003  Maeda ................. A61B 1/0016
                                                      600/146

(Continued)

FOREIGN PATENT DOCUMENTS

JP    2000-157485    6/2000
JP    2001-149302    6/2001

(Continued)

OTHER PUBLICATIONS

International Search Report, Date of mailing: May 16, 2017 (May 16, 2017) 4 pages.

*Primary Examiner* — Ryan N Henderson
(74) *Attorney, Agent, or Firm* — Rankin, Hill & Clark LLP

(57) ABSTRACT

Provided is an endoscope holder capable of turning or swinging an endoscope inserted into a body with the endoscope fixed at a predetermined insertion position. An endoscope holder (1) includes a holder main body (3) having an insertion hole (2), gripping members (7a) and (7b) configured to pinch an endoscope E inserted into the insertion hole (2), first elastic members (12a) and (12b) configured to urge in a direction in which the gripping members (7a) and (7b) are separated from each other, a pressing member (13) configure to press the gripping member (7a) toward the (Continued)

gripping member (7b), a switching mechanism (17) configured to hold or release a pressing state, rollers (10) provided in gripping members (7a) and (7b), and a second elastic member (15) configured to swingably support the gripping member (7b).

8 Claims, 13 Drawing Sheets

(58) Field of Classification Search
CPC .............. A61B 1/00147; A61B 1/0016; A61B 1/00066; A61B 2034/301; A61B 1/01; A61M 25/0105; A61M 25/0116; F16B 2/16
See application file for complete search history.

(56) References Cited

U.S. PATENT DOCUMENTS

| | | | | |
|---|---|---|---|---|
| 6,689,130 | B2* | 2/2004 | Arai | A61B 18/1492 606/46 |
| 6,981,945 | B1* | 1/2006 | Sarvazyan | A61B 1/31 606/1 |
| 7,566,300 | B2* | 7/2009 | Devierre | A61B 1/00128 600/106 |
| 7,575,548 | B2* | 8/2009 | Takemoto | A61B 1/018 600/122 |
| D612,045 | S* | 3/2010 | Sarvazyan | D24/133 |
| 7,871,371 | B2* | 1/2011 | Komiya | A61B 1/018 600/114 |
| 8,033,991 | B2* | 10/2011 | Sarvazyan | A61B 1/31 600/101 |
| 8,187,172 | B2* | 5/2012 | Skerven | A61B 1/273 600/129 |
| 8,333,689 | B2* | 12/2012 | Okamoto | A61B 1/01 600/102 |
| 8,388,518 | B2* | 3/2013 | Sarvazyan | A61B 1/00147 600/101 |
| 8,409,079 | B2* | 4/2013 | Okamoto | A61B 1/009 600/152 |
| 8,550,984 | B2* | 10/2013 | Takemoto | A61B 1/00066 600/125 |
| 8,684,912 | B2* | 4/2014 | Deviere | A61B 1/00087 600/129 |
| 8,894,567 | B2* | 11/2014 | Honda | A61B 1/00078 600/114 |
| 8,986,195 | B2* | 3/2015 | Okamoto | A61B 1/00142 600/116 |
| 9,307,891 | B2* | 4/2016 | Carter | A61B 1/00042 |
| 9,706,907 | B2* | 7/2017 | Gumbs | A61B 1/00133 |
| 9,707,376 | B2* | 7/2017 | Smith | B25B 13/5041 |
| 2002/0103418 | A1* | 8/2002 | Maeda | A61B 1/0016 600/152 |
| 2003/0212308 | A1* | 11/2003 | Bendall | A61B 1/00052 600/102 |
| 2005/0228228 | A1* | 10/2005 | Boulais | A61B 1/00147 600/137 |
| 2005/0234297 | A1* | 10/2005 | Devierre | A61B 1/00087 600/129 |
| 2006/0041245 | A1* | 2/2006 | Ferry | A61B 17/3403 604/95.01 |
| 2006/0161043 | A1* | 7/2006 | Neumann | A61B 1/00133 600/101 |
| 2007/0060879 | A1* | 3/2007 | Weitzner | A61M 25/1011 604/95.04 |
| 2007/0100201 | A1* | 5/2007 | Komiya | A61B 1/00133 600/106 |
| 2007/0265493 | A1* | 11/2007 | Zirps | A61B 17/12013 606/140 |
| 2007/0265497 | A1* | 11/2007 | Brown | A61B 1/24 600/101 |
| 2008/0045892 | A1* | 2/2008 | Ferry | A61M 25/0113 604/95.01 |
| 2008/0103357 | A1* | 5/2008 | Zeiner | A61B 1/00087 600/129 |
| 2008/0262293 | A1* | 10/2008 | Murakami | A61B 90/50 600/101 |
| 2008/0277853 | A1* | 11/2008 | Menn | A61B 17/29 600/104 |
| 2008/0287739 | A1* | 11/2008 | Smith | B25B 25/00 600/131 |
| 2009/0105539 | A1* | 4/2009 | Skerven | A61B 1/0008 600/114 |
| 2009/0247827 | A1* | 10/2009 | Secrest | A61B 1/0014 600/131 |
| 2009/0287053 | A1* | 11/2009 | Okamoto | A61B 1/00142 600/139 |
| 2010/0234873 | A1* | 9/2010 | Nagano | G01L 5/0038 254/133 R |
| 2010/0274078 | A1* | 10/2010 | Kim | A61B 34/30 600/102 |
| 2011/0077681 | A1* | 3/2011 | Nagano | A61B 17/12022 606/200 |
| 2011/0208000 | A1* | 8/2011 | Honda | A61B 1/0016 600/118 |
| 2011/0264038 | A1* | 10/2011 | Fujimoto | A61M 25/09041 604/95.01 |
| 2012/0029286 | A1* | 2/2012 | Sarvazyan | A61B 1/0052 600/131 |
| 2012/0203168 | A1* | 8/2012 | Fujimoto | G01L 5/105 604/95.01 |
| 2013/0123580 | A1* | 5/2013 | Peters | A61B 1/0016 604/95.04 |
| 2013/0261391 | A1* | 10/2013 | Dejima | A61B 1/0016 600/114 |
| 2013/0310646 | A1* | 11/2013 | Dejima | A61B 1/00148 600/114 |
| 2014/0378761 | A1* | 12/2014 | Zorn | A61B 34/70 600/104 |
| 2015/0112141 | A1* | 4/2015 | Oginski | A61B 1/00195 600/136 |
| 2016/0206849 | A1* | 7/2016 | Rykhus, Jr. | A61B 1/0014 |

FOREIGN PATENT DOCUMENTS

| | | |
|---|---|---|
| JP | 2008-113697 | 5/2008 |
| JP | 2008-154758 | 7/2008 |
| JP | 2015-198933 | 11/2015 |

* cited by examiner

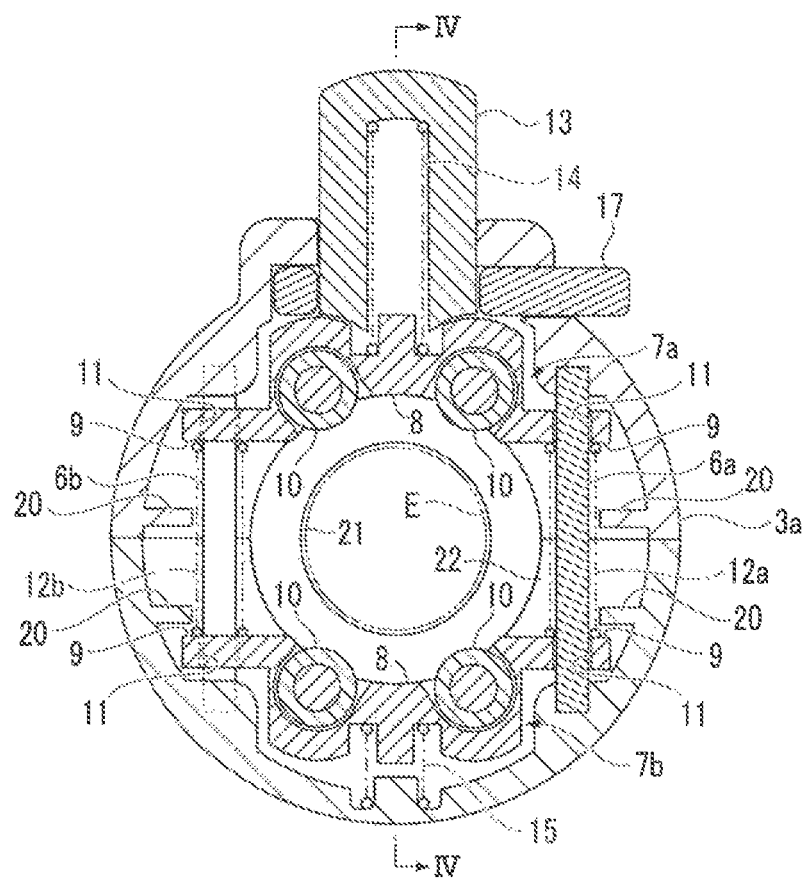

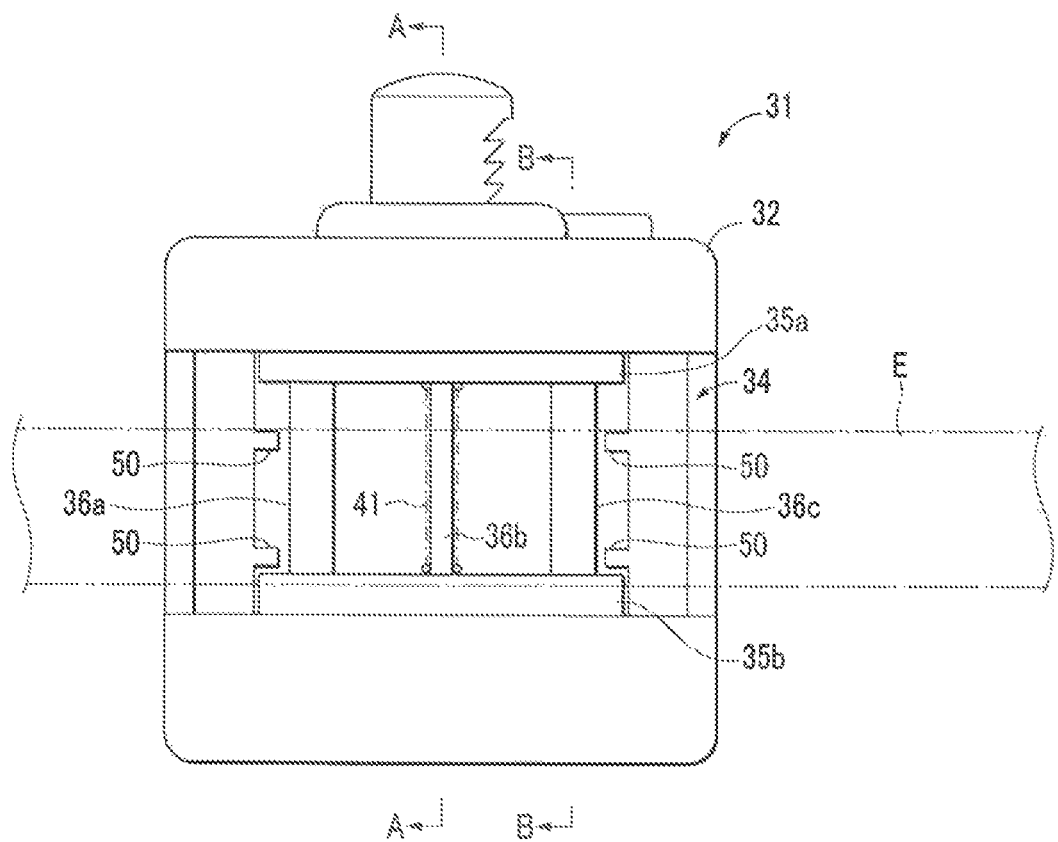

ENDOSCOPE HOLDER

TECHNICAL FIELD

The present invention relates to an endoscope holder.

BACKGROUND ART

There has been known an endoscope holder configured to fix and hold an endoscope inserted into a body at a predetermined insertion position, which includes a pair of semi-cylindrical clips openably and closably provided at a distal end of a manipulating portion and a plurality of rollers being rotatably provided at inner surfaces of the clips and extending in the lengthwise direction (see Patent Literature 1).

It is preferable that the endoscope is fixed at a predetermined insertion position when the endoscope is inserted into the body to observe the inside of the body at the insertion position or perform a required treatment. The conventional endoscope holder pinches and grips the endoscope inserted into the body with the pair of semi-cylindrical clips, whereby the endoscope holder can fix and hold the endoscope at the predetermined insertion position.

It may be preferable that the endoscope is turned in a state in which the endoscope is fixed at the insertion position, in order to observe the surroundings of the insertion position or to perform the required treatment. At this time, since the conventional endoscope holder includes the plurality of rollers which are rotatably provided at an inner surface of the clip, the endoscope which is fixed at the insertion position can be turned by the rollers.

CITATION LIST

Patent Literature

Patent Literature 1: Japanese Patent Application Laid-Open No. 2015-198933

SUMMARY OF INVENTION

Technical Problem

It is preferable that the endoscope swing relative to an axial direction in a state in which the endoscope is fixed at the insertion position, so that the distal end of the endoscope approaches an intestinal wall, a stomach wall, or the like.

In view of the above-described circumstances, an object of the present invention is to provide an endoscope holder which can turnably fix and hold an endoscope inserted into a body at a predetermined insertion position, and can swing the endoscope in a state fixed at the insertion position.

Furthermore, another object of the present invention is to provide an endoscope holder which can be easily attached to an endoscope.

Solution to Problem

To achieve such objects, an endoscope holder of a first aspect of the present invention is an endoscope holder which fixes and holds an endoscope inserted into a body at a predetermined insertion position, the endoscope holder comprising a hollow cylindrical holder main body which comprises an insertion hole into which the endoscope is to be inserted, first and second gripping members each having a plate-like body extending in a lengthwise direction of the insertion hole, and contacts the endoscope inserted into the insertion hole to pinch the endoscope, a first elastic member which is disposed between the first and second gripping members and urges the first and second gripping members in a direction in which the first and second gripping members are separated from each other, a pressing member which presses the first gripping member toward the second gripping member against an urging force of the first elastic member, a switching mechanism which holds or releases a pressing state by the pressing member, rollers which are rotatably provided at surfaces of the first and second gripping members which are in contact with the endoscope, along the lengthwise direction of the insertion hole, and a second elastic member which is provided between the second gripping member and an inner wall of the insertion hole, and swingably supports the second gripping member with respect to the lengthwise direction of the insertion hole.

In the endoscope holder of the first aspect of the present invention, the first and second gripping members each having a plate-like body extending in a lengthwise direction of the insertion hole are provided in the insertion hole of the hollow cylindrical holder main body, and the first elastic member urging in a direction in which the first and second gripping members are separated from each other is disposed between the first and second gripping members. The first gripping member is pressed by the pressing member toward the second gripping member against the urging force of the first elastic member, thereby pinching the endoscope between the first gripping member and the second gripping member. The pressing state by the pressing member is maintained by the switching mechanism, resulting that the endoscope holder of the present invention can hold the endoscope between the first and second gripping members, thereby capable of fixing the endoscope inserted into the body at the predetermined insertion position.

At this time, the first and second gripping members are provided with the rollers in the surfaces which are in contact along the endoscope, in the lengthwise direction of the insertion hole, and the rollers are rotatable. The rollers enable the endoscope pinched between the first and second gripping members to be turned in a state in which the endoscope is fixed at the predetermined insertion position in the body.

At this time, the second gripping member is swingably held in the lengthwise direction of the insertion hole by the second elastic member disposed between the inner wall of the insertion hole and the second gripping member. Accordingly, the endoscope pinched between the first and second gripping members can swing, together with the first and second gripping members, in the lengthwise direction of the insertion hole, in other words, in an axial direction of the endoscope, in a state in which the endoscope is fixed at the predetermined insertion position in the body.

When the pressing state by the pressing member is released by the switching mechanism, the first gripping member can be returned to the original position by the urging force of the first elastic member.

The endoscope holder of the first aspect of the present invention may comprise a third elastic member which is disposed between the first gripping member and the pressing member and swingably supports the first gripping member with respect to the lengthwise direction of the insertion hole.

According to this configuration, the first gripping member is also swingably held in the lengthwise direction of the insertion hole by the third elastic member disposed between the pressing member and the first gripping member, so that the endoscope pinched between the first and second gripping members can readily swing in the lengthwise direction of the insertion hole together with the first and second gripping members.

In the endoscope holder of the first aspect of the present invention, a plurality of the second elastic members are preferably disposed in at least two positions along the lengthwise direction of the insertion hole. The second elastic members are disposed in at least two positions in the lengthwise direction of the insertion hole, thereby enabling the second gripping member to stably swing.

The endoscope holder of the first aspect of the present invention preferably comprises a restricting member on an inner wall surface of the insertion hole, the restricting member restricting mutual approach between the first and second gripping members. The endoscope holder of the present invention comprises the restricting member on the inner wall surface of the insertion hole, thereby enabling the endoscope to be prevented from being excessively firmly pinched between the first and second gripping members to thereby prevent the endoscope from being damaged.

It is preferable that the endoscope holder of the first aspect of the present invention comprise at least a pair of columnar members in the insertion hole, the columnar members being erected on opposite sides of a center axis of the insertion hole, and the first and second gripping members comprise hole portions into which the columnar members are to be inserted, and the hole portions each have at least a gap in the lengthwise direction of the insertion hole with respect to the columnar member.

The first and second gripping members comprise the hole portions, and the columnar members are inserted in the hole portions, so that the first and second gripping members can be moved along the columnar members when being pressed by the pressing member or being released from pressing.

On the other hand, when the first and second gripping members swing as described above, the first and second gripping members may be prevented from swinging due to the interference with the columnar members. However, in the endoscope holder of the first aspect of the present invention, the hole portions each have at least a gap in the lengthwise direction of the insertion hole with respect to the columnar member, thereby capable of preventing the columnar members from interfering with the first and second gripping member even when the first and second gripping member swing.

The endoscope holder of the first aspect of the present invention preferably comprises a fixing member which is provided on an outer peripheral surface of a distal end of the holder main body and detachably fixes the holder main body to a mouth piece. The endoscope holder of the first aspect of the present invention is fixed to the mouth piece by the fixing member, and is thereby capable of holding the endoscope inserted into the body through the mouth piece.

The endoscope holder of the first aspect of the present invention may have a deaeration preventing valve which seals between the endoscope inserted into the insertion hole and an inner wall of the insertion hole. According to this configuration, the deaeration preventing valve prevents deaeration from the body into which the endoscope is inserted, thereby capable of always maintaining good observation field of view of the endoscope in the body.

An endoscope holder of a second aspect of the present invention is an endoscope holder which fixes and holds an endoscope inserted into a body at a predetermined insertion position, the endoscope holder comprising a holder main body having a hollow square cylindrical shape which comprises an endoscope housing part with an opening in one side surface thereof, the endoscope housing part being configured to house the endoscope therein, first and second gripping members each having a plate-like body extending in a lengthwise direction of the endoscope housing part, and contacts the endoscope housed in the endoscope housing part to pinch the endoscope, a first elastic member which is disposed between the first and second gripping members and urges the first and second gripping members in a direction in which the first and second gripping members are separated from each other, a pressing member which presses the first gripping member toward the second gripping member against an urging force of the first elastic member, a switching mechanism which holds or releases a pressing state by the pressing member, rollers which are rotatably provided at surfaces of the first and second gripping members which are in contact with the endoscope, along the lengthwise direction of the endoscope housing part, and a second elastic member which is provided between the second gripping member and an inner wall of the endoscope housing part, and swingably supports the second gripping member in the lengthwise direction of the endoscope housing part.

For example, when the endoscope holder comprises a holder main body made of a hollow square cylindrical body but having no opening in one side surface thereof, the endoscope holder must be mounted to the endoscope by inserting the long endoscope into the holder main body from a distal end of the endoscope. In contrast, the endoscope holder of the present invention comprises a holder main body having a hollow square cylindrical shape and an opening in one side surface thereof, and an endoscope housing part configured to house the endoscope therein. According to the endoscope holder of the present invention, an opened side surface of the holder main body is set parallel to arbitrary portion in the lengthwise direction of the endoscope, and the endoscope is housed in the endoscope housing part from the opened side surface, thereby capably of easily mounting the endoscope holder to the long endoscope.

In the endoscope holder of the second aspect of the present invention, the first and second gripping members each having a plate-like body extending in a lengthwise direction of the endoscope housing part are provided in the endoscope housing part of the holder main body, and the first elastic member urging in a direction in which the first and second gripping members are separated from each other is disposed between the first and second gripping members. The first gripping member is pressed by the pressing member toward the second gripping member against the urging force of the first elastic member, thereby pinching the endoscope between the first gripping member and the second gripping member. The pressing state by the pressing member is maintained by the switching mechanism, resulting that the endoscope holder of the second aspect of the present invention can hold the endoscope between the first and second gripping members, thereby capable of fixing the endoscope inserted into the body at the predetermined insertion position.

At this time, the first and second gripping members are provided with the rollers in the surfaces which are in contact along the endoscope, in the lengthwise direction of the endoscope housing part, and the rollers are rotatable. The rollers enable the endoscope held between the first and second gripping members to be turned in a state in which the endoscope is fixed at the predetermined insertion position in the body.

At this time, the second gripping member is swingably held in the lengthwise direction of the endoscope housing part by the second elastic member disposed between the inner wall of the endoscope housing part and the second gripping member. Accordingly, the endoscope held between the first and second gripping members can swing in the lengthwise direction of the endoscope housing part, in other words, in an axial direction of the endoscope, in a state in which the endoscope is fixed at the predetermined insertion position in the body.

In the endoscope holder of the second aspect of the present invention, when the pressing state by the pressing member is released by the switching mechanism, the first gripping member can be returned to the original position by the urging force of the first elastic member.

The endoscope holder of the second aspect of the present invention preferably comprises a third elastic member which is disposed between the first gripping member and the pressing member and swingably supports the first gripping member with respect to the lengthwise direction of the endoscope housing part.

In the endoscope holder of the second aspect of the present invention, a plurality of the second elastic members are preferably disposed in at least two positions along the lengthwise direction of the endoscope housing part. The second elastic members are disposed in at least two positions in the lengthwise direction of the endoscope housing part, thereby enabling the second gripping member to stably swing.

The endoscope holder of the second aspect of the present invention comprises the third elastic member, and thereby the first gripping member is also swingably held in the lengthwise direction of the endoscope housing part, so that the endoscope held between the first and second gripping members can readily swing along the lengthwise direction of the endoscope housing part.

The endoscope holder of the second aspect of the present invention preferably comprises a restricting member on an inner wall surface of the endoscope housing part, the restricting member restricting mutual approach between the first and second gripping members. The endoscope holder of the second aspect of the present invention comprises the restricting member on the inner wall surface of the endoscope housing part, thereby enabling the endoscope to be prevented from being excessively firmly pinched between the first and second gripping members to thereby prevent the endoscope from being damaged.

It is preferable that the endoscope holder of the second aspect of the present invention comprise a plurality of columnar members erected along a side surface facing the opened side surface of the endoscope housing part, and the first and second gripping members comprise oblong hole portions into which the columnar members are to be inserted, and the oblong hole portions each have at least a gap in the lengthwise direction of the endoscope housing part with respect to the columnar member.

The first and second gripping members comprise the oblong hole portions, and the columnar members are inserted in the oblong hole portions, so that the first and second gripping members can be moved along the columnar members when being pressed by the pressing member or being released from pressing.

On the other hand, when the first and second gripping members swing as described above, the first and second gripping members may be prevented from swinging due to the interference with the columnar members. However, in the endoscope holder of the second aspect of the present invention, the oblong hole portions each have at least a gap in the lengthwise direction of the endoscope housing part with respect to the columnar member, thereby capable of preventing the columnar members from interfering with the first and second gripping member even when the first and second gripping member swing.

The endoscope holder of any one of aspects of the present invention comprises an arm supporting the holder main body at an arbitrary position and posture, and the holder main body may be integrally fixed to a distal end of the arm or detachably attached to the distal end. According to this configuration, the endoscope holder is supported by the arm at an arbitrary position and posture, thereby capable of holding the endoscope at appropriate position and posture corresponding to various conditions.

In this case, the endoscope holder of any one of aspects of the present invention may have an arm fixing unit configured to detachably fix a proximal end of the arm to a frame or a rail part of a bed or another fixing member. Thus, the arm is fixed to the bed or the like, thereby capable of holding the holder main body by the arm at an arbitrary position in a space on the bed at an arbitrary posture. Accordingly, the endoscope can be held at appropriate position and posture corresponding to various conditions of a patient undergoing a procedure on the bed.

The endoscope holder of any one of aspects of the present invention may hold a large intestine endoscope as an endoscope held by the endoscope holder. According to this, while the large intestine endoscope is appropriately held as described above, an examination can be performed on a patient on the bed with the large intestine endoscope.

BRIEF DESCRIPTION OF DRAWINGS

FIG. 3 is a cross-sectional view taken along line III-III of FIG. 2A.

FIG. 8 is a side view illustrating the endoscope holder illustrated in FIG. 7 as viewed from a direction from an opening.

FIG. 7 is used for a large intestine endoscope using an arm.

DESCRIPTION OF EMBODIMENTS

Hereinafter, embodiments of the present invention will be described in further detail with reference to the accompanying drawings.

First, an endoscope holder 1 of a first aspect of the present embodiment will be described with reference to FIGS. 1 to 6.

Figure 1:
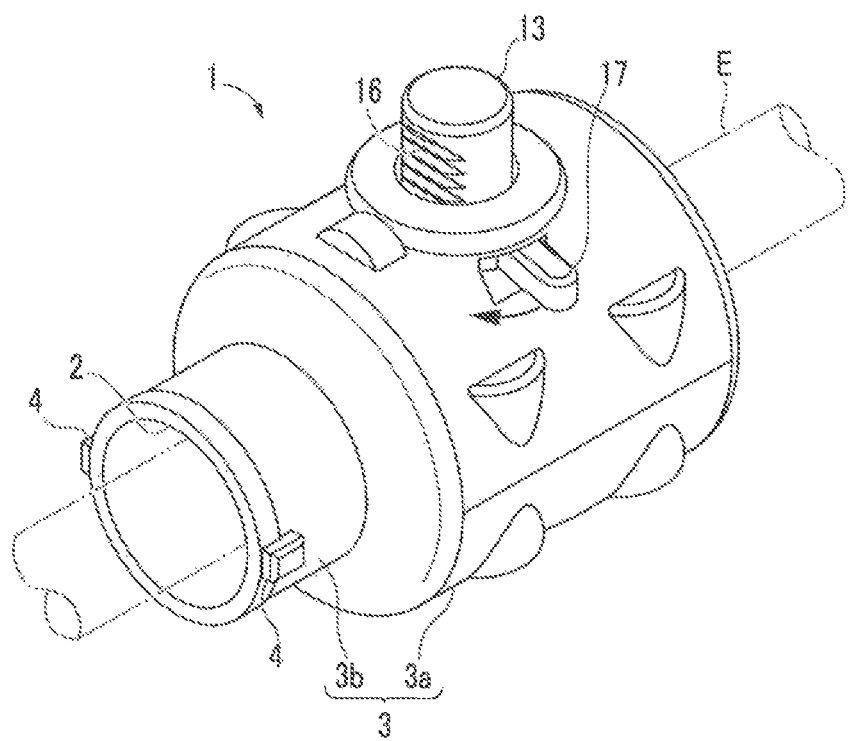
FIG. 1 is a perspective view illustrating a configuration of an endoscope holder of a first aspect of the present invention.

As illustrated in FIG. 1, the endoscope holder 1 of the first aspect of the present embodiment includes a hollow cylindrical holder main body 3 comprising an insertion hole 2 into which an endoscope E is to be inserted. The holder main body 3 includes a larger diameter part 3a, and a smaller diameter part 3b protruding from a distal end of the larger diameter part 3a, and the insertion hole 2 passes through the larger diameter part 3a and the smaller diameter part 3b. A pair of protruding fixing members 4 are provided at the distal end of the smaller diameter part 3b.

Figure 2A:
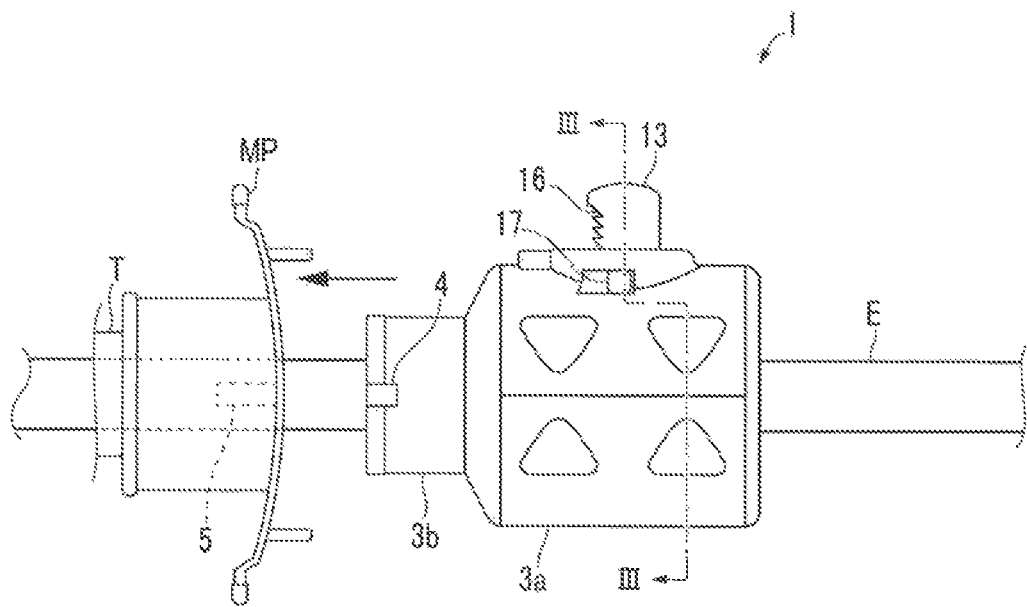
FIG. 2A is a side view illustrating a state before the endoscope holder illustrated in FIG. 1 is fixed to a mouth piece.

As illustrated in FIG. 2A, for example, the endoscope E is inserted into a predetermined position in the body through a mouth piece MP and an over tube T connected to the mouth piece MP. At this time, the endoscope holder 1 with the endoscope E inserted into the insertion hole 2 is moved toward the mouth piece MP as indicated by an arrow.

Figure 2B:
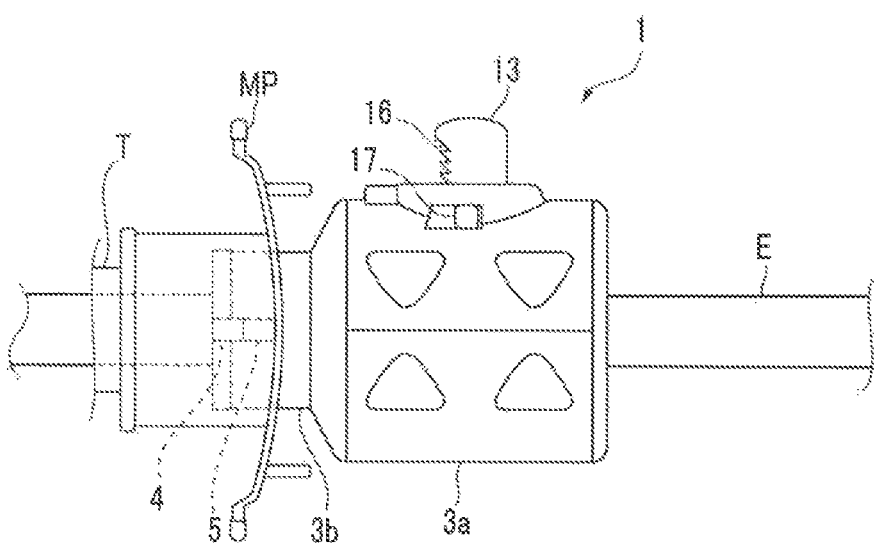
FIG. 2B is a side view illustrating a state after the endoscope holder illustrated in FIG. 1 is fixed to the mouth piece.

Thus, as illustrated in FIG. 2B, the pair of protruding fixing members 4 provided at the distal end of the smaller diameter part 3b of the holder main body 3 are fitted into recessed portions 5 provided in the mouth piece MP, respectively, so that the endoscope holder 1 can be detachably fixed to the mouth piece MP.

Note that, in the endoscope holder 1 of the present embodiment, the mouth piece MP is not used when the endoscope E is a lower portion (large intestine) endoscope as described later.

Figure 4:
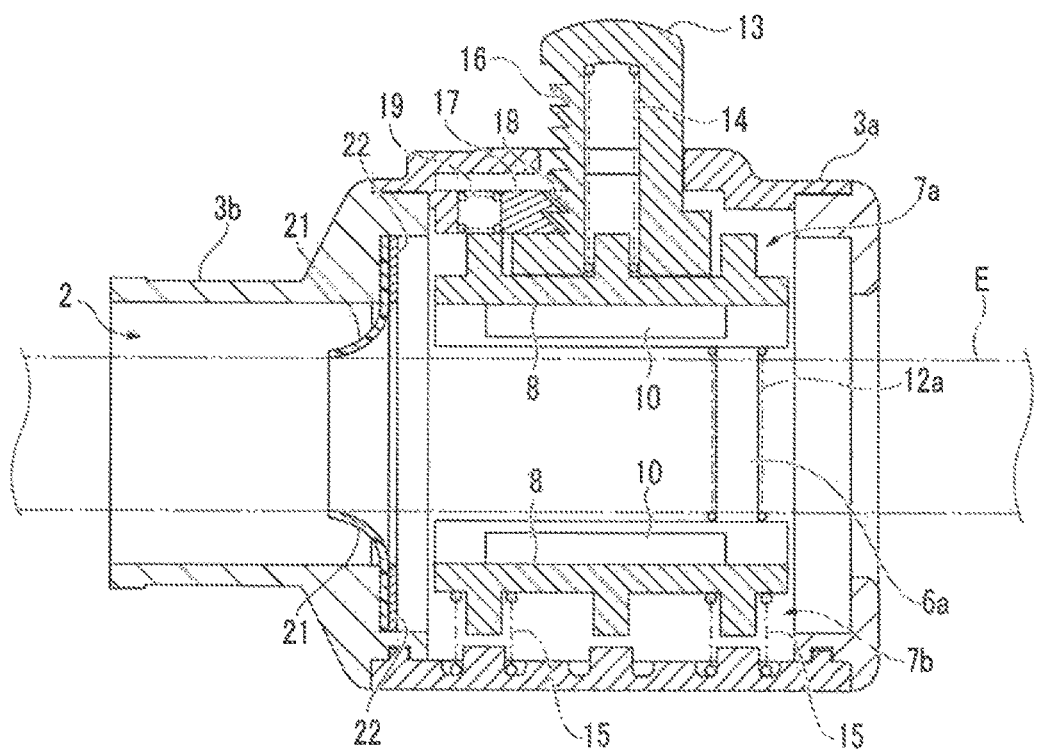
FIG. 4 is a cross-sectional view taken along line IV-IV of FIG. 3.

As illustrated in FIG. 3 and FIG. 4, the endoscope holder 1 of the present embodiment comprises a pair of columnar members 6a and 6b erected on opposite sides of a center axis in the insertion hole 2, and first and second gripping members 7a and 7b each having a plate-like body extending in a lengthwise direction of the insertion hole 2. As illustrated in FIG. 3, each of the first and second gripping members 7a and 7b comprises a surface 8 having a circular arc shape in a cross-sectional view, and flat plate-shaped surfaces 9 continuously connected to both ends of the circular arc surface 8, so that the circular arc surfaces 8 are in contact along the endoscope E, each of the circular arc surfaces 8 comprising a pair of rollers 10 which are rotatably provided in the lengthwise direction of the insertion hole 2.

Hole portions 11 are provided in the flat plate-shaped surfaces 9, and each of the columnar members 6a and 6b is inserted into the corresponding hole portion 11. As a result, the first and second gripping members 7a and 7b can be moved along the columnar members 6a and 6b.

Figure 5:
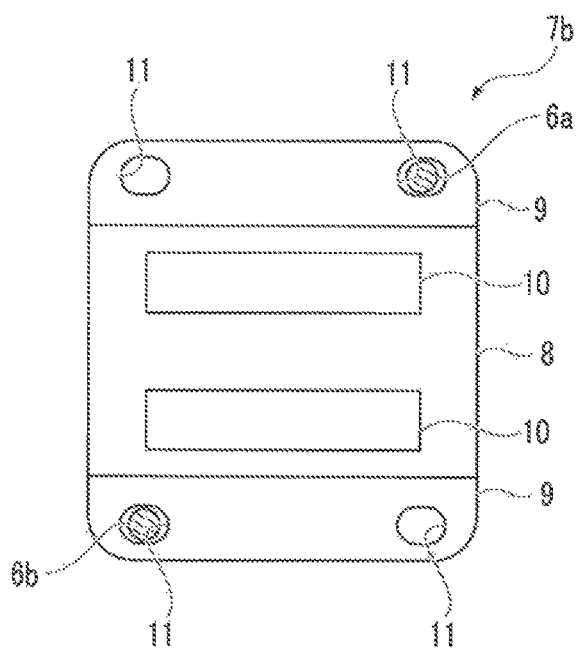
FIG. 5 is a planar view of a gripping member illustrated in FIG. 3.
Figure 6:
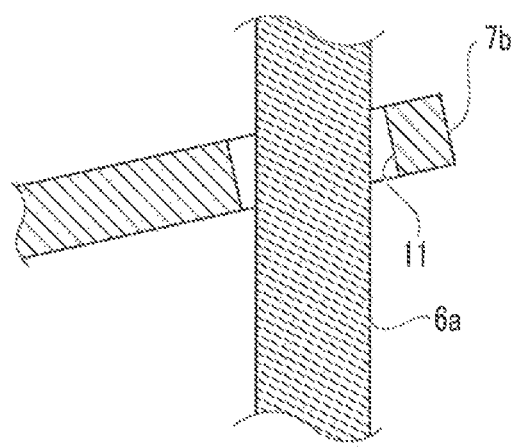
FIG. 6 is a schematic cross-sectional view illustrating a state in which the gripping member illustrated in FIG. 3 swings.

Note that, in FIG. 5, the hole portions 11 each are an oblong hole extending in the lengthwise direction of the insertion hole 2, but it is only required that the hole portions 11 each are provided with at least a gap in the lengthwise direction of the insertion hole 2 with respect to the columnar members 6a and 6b, and the hole portions 11 each may be a circular hole having a gap over the entire circumference of the columnar members 6a and 6b. When the hole portion 11 is an oblong hole, the hole portion 11 may have a gap with respect to the columnar member 6a or 6b to be inserted, the gap having the narrowest width at a center portion in the thickness direction of the first and second gripping members 7a and 7b, and a shape (an X shape, or a V shape in the upper half and an inverted V shape in the lower half) gradually expanding toward a surface of the gripping member from the center portion, in a cross-sectional view in the lengthwise direction of the insertion hole 2.

Springs 12a and 12b are disposed with the respective columnar members 6a and 6b as axes between the first and second gripping members 7a and 7b, each of the springs 12a and 12b serving as a first elastic member urging in a direction in which the first and second gripping members 7a and 7b are separated from each other.

The first gripping member 7a is connected to a pressing member 13 provided penetrating a side wall of the larger diameter part 3a of the holder main body 3, through a spring 14 serving as a third elastic member. The spring 14 is incorporated in the pressing member 13. Here, the first gripping member 7a is adapted to be pressed by the pressing member 13 toward the second gripping member 7b against urging forces of the springs 12a and 12b. Note that the spring 14 is not necessary, and may not be provided.

On the other hand, the second gripping member 7b is held by springs 15 serving as second elastic members which are disposed between the second gripping member 7b and an inner wall surface of the larger diameter part 3a of the holder main body 3. As illustrated in FIG. 4, in the present embodiment, the two springs 15 are provided along the lengthwise direction of the insertion hole 2, but the number of springs 15 may be one or three or more.

For example, the pressing member 13 can maintain a pressing state of pressing the first gripping member 7a toward the second gripping member 7b by a ratchet mechanism by which a rack 16 provided on a side surface of the pressing member 13 is engaged with pawls 18 provided to a lever 17 serving as a switching mechanism. The lever 17 is urged by a spring 19 toward the pressing member 13. In the ratchet mechanism, when the pressing member 13 is pressed down, the rack 16 presses the pawls 18 so that the pawls 18 is evacuated in a direction away from the pressing member 13, and when the rack 16 passes through the pawls 18, the pawls 18 is moved toward the pressing member 13 again to be engaged with the rack 16.

When the lever 17 is operated in a direction away from the pressing member 13 against the urging force of the spring 19 as indicated by an arrow in FIG. 1, the engagement between the pawls 18 and the rack 16 is released, which enables the pressing state of the first gripping member 7a to be released.

In the present embodiment, the pressing member 13 and the switching mechanism are implemented by the ratchet mechanism, but may be implemented by a so-called two-step knock mechanism (for example, see Japanese Patent Laid-Open No. 9-99691), a heart cam mechanism (for example, see Japanese Patent Laid-Open No. 2014-11068), or the like.

As illustrated by way of example for the second gripping member 7b in FIG. 5, the two hole portions 11 are provided in the front-rear direction in each of the flat plate-shaped surfaces 9 which are connected to both ends of the circular arc surface 8, so that the hole portions 11 are provided at four positions in total. In the present embodiment, the columnar members 6a and 6b are separately inserted into one hole portion each in the flat plate-shaped surfaces 9, with respect to the above-described four hole portions 11, so as to be placed in a diagonal direction, so that the pair of columnar members 6a and 6b are disposed with the center axis in between in a front view. However, the columnar members 6a and 6b may be separately inserted into the four hole portions 11, so that the number of columnar members 6a and 6b is four in total.

Note that in the endoscope holder 1 of the first aspect of the present embodiment, stoppers 20 may be provided between the first and second gripping members 7a and 7b, in a manner protruding from the inner wall surface of the larger diameter part 3a of the holder main body 3, so that the stoppers 20 restrict, as restricting members, the approach between the first and second gripping members 7a and 7b. Providing the stoppers 20 enables the endoscope E to be prevented from being excessively firmly pinched between the first and second gripping members 7a and 7b, thereby capable of preventing the endoscope E from being damaged. The stoppers 20 may extend a predetermined length along the lengthwise direction of the insertion hole 2, or may be intermittently provided in place along the lengthwise direction of the insertion hole 2.

The endoscope holder 1 may have a deaeration preventing valve 21 which prevents deaeration from the body to be observed by the endoscope E to secure good observation field of view. As illustrated in FIG. 4, for example, the deaeration preventing valve 21 can be fixed between a surface forming a step at a rear end of the smaller diameter part 3b where the diameter is increased and a fixing annular member 22 by press-fitting or welding.

The deaeration preventing valve 21 is configured to have an opening at a center thereof through which the endoscope E passes when the endoscope E is inserted into the insertion hole 2, and has a function of sealing between the inserted endoscope E and the insertion hole 2.

Next, the operation of the endoscope holder 1 of the first aspect of the present embodiment will be described.

The endoscope holder 1 of the present embodiment is used in a state where the endoscope E which has been inserted into a predetermined position in the body through the mouth piece MP and the over tube T is inserted into the insertion hole 2, for example. At this time, as illustrated in FIG. 2B, the fixing members 4 are fitted into the recessed portions 5 provided in the mouth piece MP, respectively, so that the endoscope holder 1 is fixed and connected to the mouth piece MP.

Next, as illustrated in FIG. 3 and FIG. 4, when the pressing member 13 is pressed down, the first and second gripping members 7a and 7b are guided by the columnar members 6a and 6b and are moved downward, and the first gripping member 7a is pressed toward the second gripping member 7b against the urging forces of the springs 12a and 12b. At this time, as described above, the rack 16 of the pressing member 13 is engaged with the pawls 18 of the lever 17, which can maintain a pressing state of pressing the first gripping member 7a toward the second gripping member 7b, resulting that the endoscope E is pinched and held between the first and second gripping members 7a and 7b. As a result, the endoscope E inserted into the body is fixed by the endoscope holder 1 at a predetermined insertion position.

At this time, the endoscope holder 1 comprises the ratchet mechanism by which the rack 16 of the pressing member 13 is engaged with the pawls 18 of the lever 17, so that the first gripping member 7a can gradually approach the second gripping member 7b. As a result, the endoscope holder 1 can securely hold the endoscope E between the first and second gripping members 7a and 7b irrespective of the size of the diameter of the endoscope E.

In the endoscope holder 1, the rollers 10 are rotatably provided on the circular arc surface 8 of each of the first and second gripping members 7a and 7b, so that the endoscope E can be turned in a state in which the endoscope E is fixed at the predetermined insertion position.

In the endoscope holder 1, the first gripping member 7a and the second gripping member 7b are swingably held, in the lengthwise direction of the insertion hole 2, by the spring 14 disposed between the pressing member 13 and the first gripping member 7a, and by the springs 15 disposed between the inner wall of the larger diameter part 3a and the second gripping member 7b, respectively. Then, the endoscope E can swing, together with the first and second gripping members 7a and 7b, in an axial direction of the endoscope E in a state in which the endoscope E is fixed at the predetermined insertion position in the body.

At this time, in the endoscope holder 1, the columnar members 6a and 6b are inserted into the hole portions 11 provided in each of the first and second gripping members 7a and 7b. Accordingly, as illustrated by way of example for the second gripping member 7b in FIG. 6, even when the first and second gripping members 7a and 7b swing, the columnar members 6a and 6b can be prevented from interfering with the first and second gripping members 7a and 7b, resulting that the first and second gripping members 7a and 7b can smoothly swing.

Note that in the present embodiment, the endoscope holder 1 is adapted to be fixed and connected to the mouth piece MP, but the endoscope holder 1 may be fixed to another instrument or the like, and is not necessarily connected to the mouth piece MP.

Next, an endoscope holder 31 of a second aspect of the present embodiment will be described with reference to FIG. 7 to FIG. 11.

Figure 7:
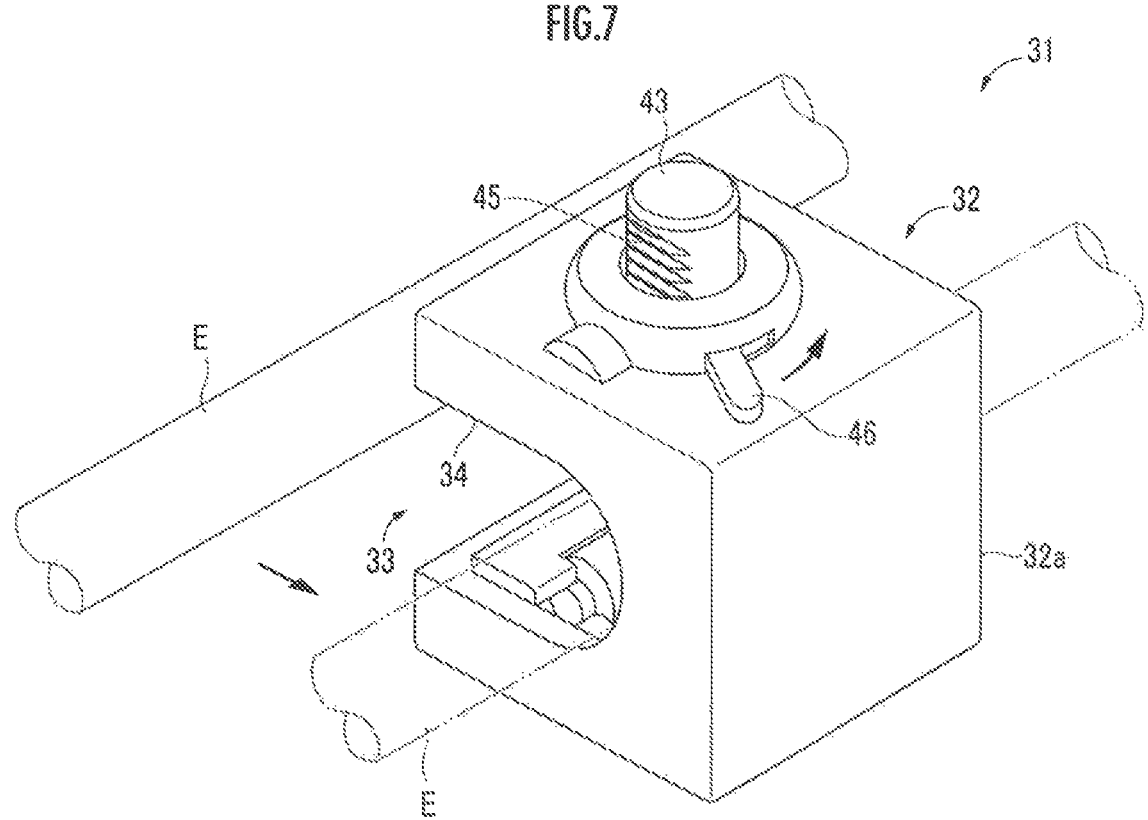
FIG. 7 is a perspective view illustrating a configuration of an endoscope holder of a second aspect of the present invention.

As illustrated in FIG. 7, the endoscope holder 31 of the second aspect of the present embodiment comprises a holder main body 32 made of a hollow square cylindrical body, and the holder main body 32 comprises an opening 33 in one side surface of the hollow square cylindrical body. The holder main body 32 comprises an endoscope housing part 34 in the hollow square cylindrical body, the endoscope housing part 34 being configured to house the endoscope E to be inserted from the opening 33.

Figure 9A:
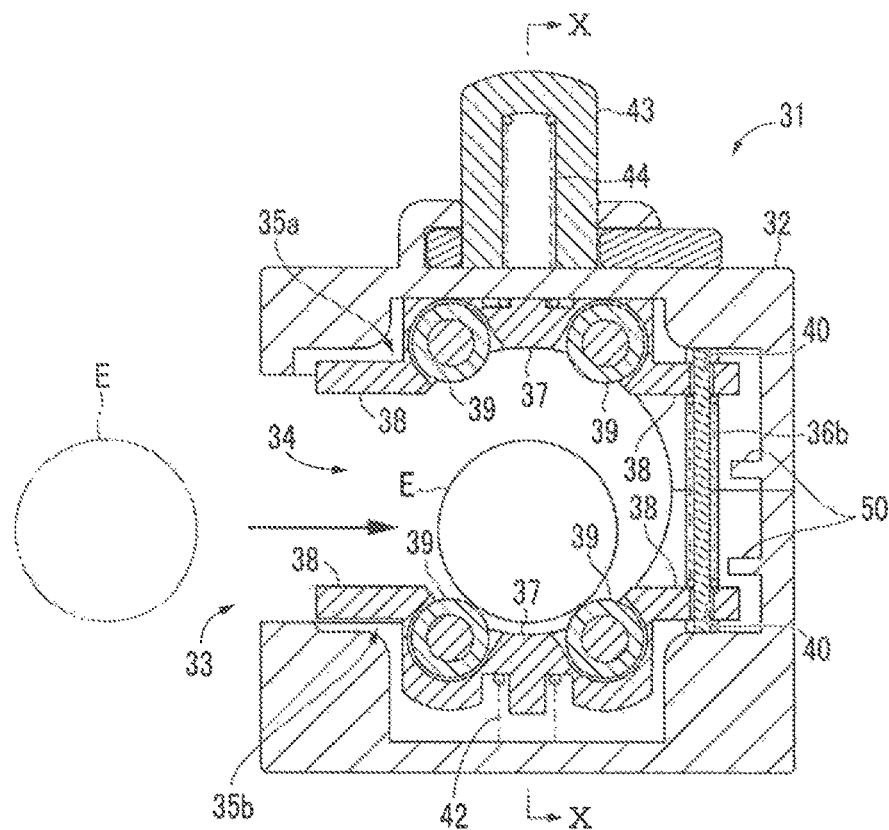
FIG. 9A is a cross-sectional view taken along line A-A of FIG. 8.
Figure 9B:
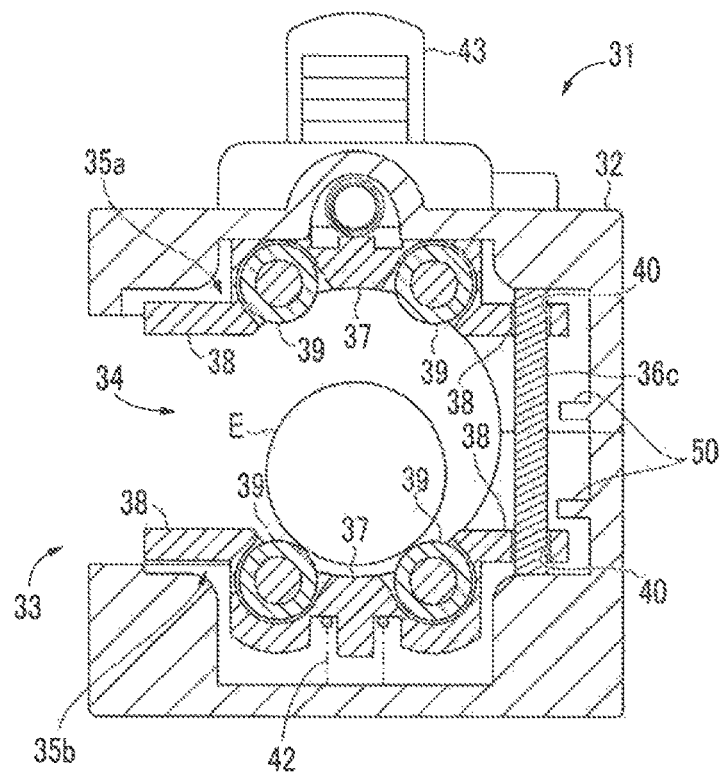
FIG. 9B is a cross-sectional view taken along line B-B of FIG. 8.
Figure 10:
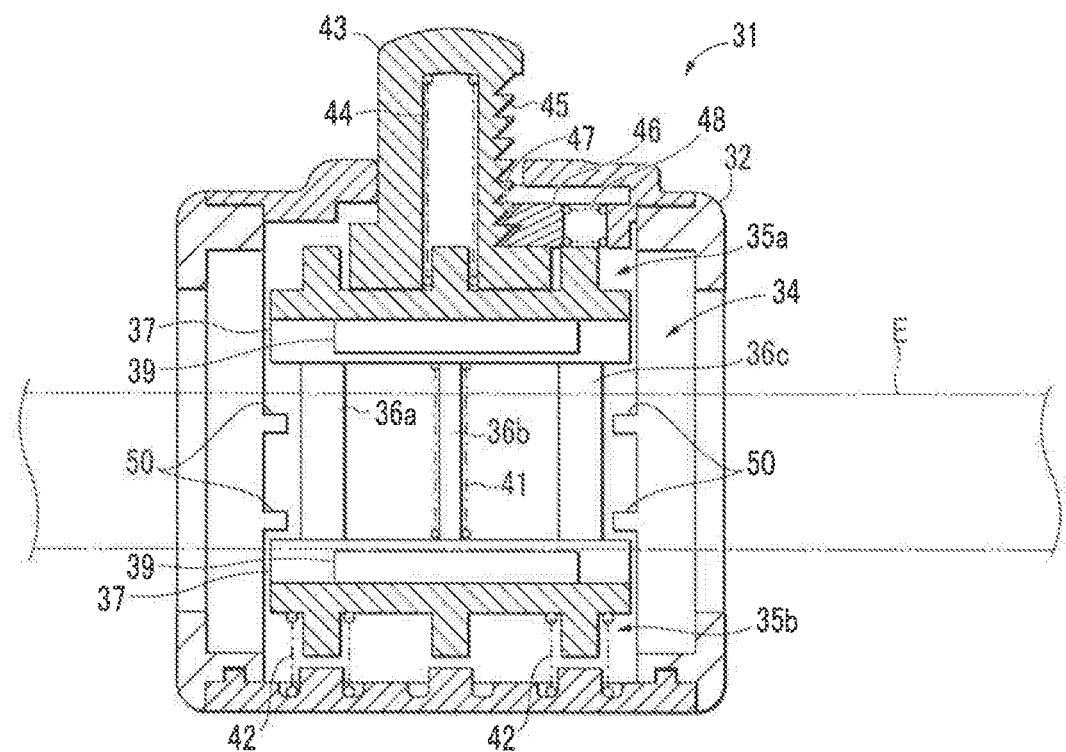
FIG. 10 is a cross-sectional view taken along line X-X of FIG. 9A.

As illustrated in FIG. 8 to FIG. 10, the endoscope holder 31 of the second aspect of the present embodiment comprises, in the endoscope housing part 34, first and second gripping members 35a and 35b each having a plate-like body extending in a lengthwise direction of the endoscope housing part 34, and three columnar members 36a, 36b, and 36c erected along a side surface 32a facing the opening 33. As illustrated in FIGS. 9A and 9B, each of the first and second gripping members 35a and 35b comprises a surface 37 having a circular arc shape in a cross-sectional view and flat plate-shaped surfaces 38 continuously connected to both ends of the circular arc surface 37, so that the circular arc surfaces 37 are in contact along the endoscope E, each of the circular arc surfaces 37 comprising a pair of rollers 39 which are rotatably provided in the lengthwise direction of the endoscope housing part 34.

An oblong hole portion 40 is provided in the flat plate-shaped surface 38, and the columnar members 36a, 36b, and 36c are inserted into the oblong hole portion 40. As a result, the first and second gripping members 35a and 35b can be moved along the columnar members 36a, 36b, and 36c.

A spring 41 is disposed with the columnar member 36b as an axis between the first and second gripping members 35a and 35b, the spring 41 serving as a first elastic member urging in a direction in which the first and second gripping members 35a and 35b are separated from each other.

The second gripping member 35b is swingably held, in the lengthwise direction of the endoscope housing part 34, by springs 42 as second elastic members which are disposed between an inner bottom wall surface of the holder main body 32 and the second gripping member 35b. As illustrated in FIG. 10, in the present embodiment, the two springs 42 are provided along the lengthwise direction of the endoscope housing part 34, but the number of springs 42 may be one or three or more.

On the other hand, the first gripping member 35a is connected to a pressing member 43 provided penetrating a top surface of the holder main body 32, through a spring 44 serving as a third elastic member, in a swingable manner in the lengthwise direction of the endoscope housing part 34. The spring 44 is incorporated in the pressing member 43. Here, the first gripping member 35a is adapted to be pressed by the pressing member 43 toward the second gripping member 35b against urging forces of the spring 44. Note that the spring 44 is not necessary, and may not be provided.

For example, the pressing member 43 can maintain a pressing state of pressing the first gripping member 35a toward the second gripping member 35b by a ratchet mechanism by which a rack 45 provided on a side surface of the pressing member 43 is engaged with pawls 47 provided to a lever 46 serving as a switching mechanism. The ratchet mechanism has the same configuration and function as that of the first aspect, and operates in the same manner as that of the first aspect.

Figure 11:
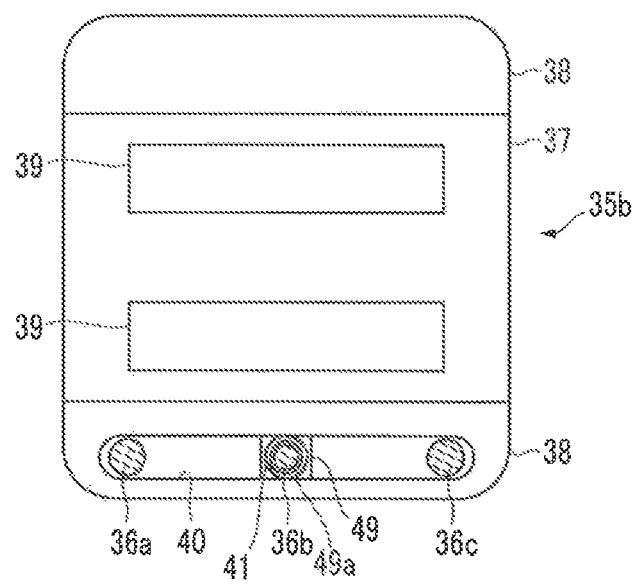
FIG. 11 is a plan view of a gripping member illustrated in FIG. 10.
Figure 12A:
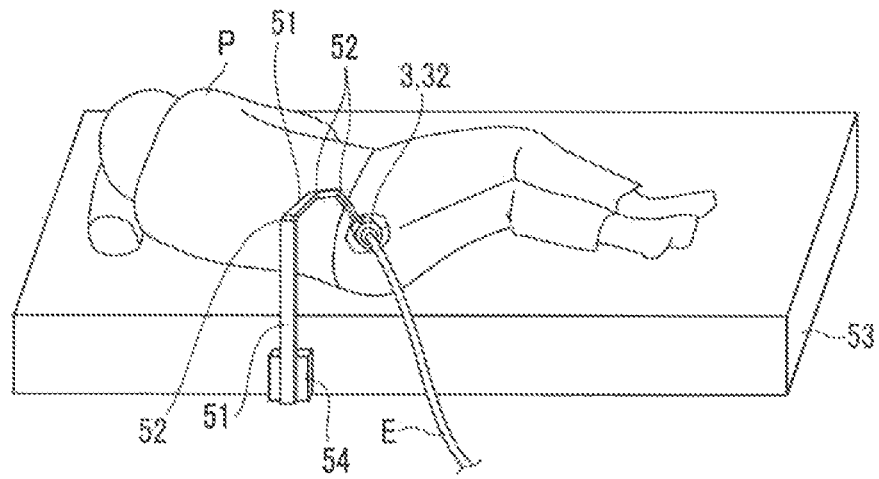
FIG. 12A is a perspective view illustrating a state in which the endoscope holder illustrated in FIG. 1
Figure 12B:
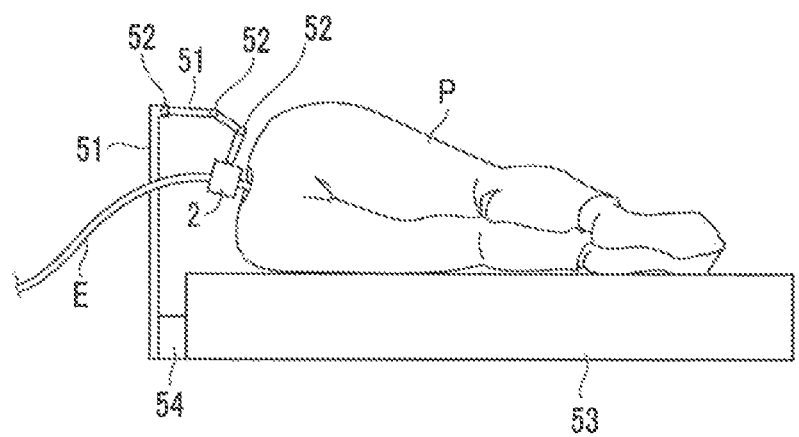
FIG. 12B is a side view of FIG. 12A as viewed from a direction from patient's feet.

As illustrated by way of example for the second gripping member 35b in FIG. 11, the oblong hole portion 40 is provided in the flat plate-shaped surface 38 on one side of the circular arc surface 37. The columnar members 36a and 36c are inserted into both ends of the oblong hole portion 40, and the oblong hole portion 40 comprises a bridging portion 49 at a center of the oblong hole portion 40. The bridging portion 49 comprises a circular hole portion 49a so that the columnar member 36b is inserted into the circular hole portion 49a, and an end of the spring 41 is engaged with the bridging portion 49. The oblong hole portion 40 has a gap around each of the columnar members 36a and 36c, and the circular hole portion 49a has a gap around the columnar member 36b.

In the holder main body 32, a pair of upper and lower stoppers 50 are provided between the first and second gripping members 35a and 35b and on each of inner surfaces of the side surface 32a in a protruding manner, so that the stoppers 50 restrict, as restricting members, the approach between the first and second gripping members 35a and 35b. The stopper 50 has the same configuration and function as the stopper 20 of the first aspect.

Next, the operation of the endoscope holder 31 of the second aspect of the present embodiment will be described.

As illustrated in FIG. 7, in the endoscope holder 31 of the present embodiment, the opening 33 of the holder main body 32 is set parallel to arbitrary portion in the lengthwise direction of the endoscope E, and the endoscope E is moved in a direction indicated by an arrow to be housed in the endoscope housing part 34 from the opening 33, so that the endoscope holder 31 is mounted to the endoscope E.

Next, when the pressing member 43 is pressed down, the first and second gripping members 35a and 35b are guided by the columnar members 36a, 36b, and 36c and are moved downward, and the first gripping member 35a is pressed toward the second gripping member 35b against the urging force of the spring 41. At this time, as in the case of the first aspect described above, the rack 45 of the pressing member 43 is engaged with the pawls 47 of the lever 46, which can maintain a pressing state of pressing the first gripping member 35a toward the second gripping member 35b, resulting that the endoscope E is pinched and held between the first and second gripping members 35a and 35b. As a result, the endoscope E inserted into the body is fixed by the endoscope holder 31 at a predetermined insertion position.

At this time, the endoscope holder 31 comprises the ratchet mechanism by which the rack 45 of the pressing member 43 is engaged with the pawls 47 of the lever 46, so that the first gripping member 35a can gradually approach the second gripping member 35b. As a result, the endoscope holder 31 can securely hold the endoscope E between the first and second gripping members 35a and 35b irrespective of the size of the diameter of the endoscope E.

In the endoscope holder 31, the rollers 39 are rotatably provided on the circular arc surface 37 of each of the first and second gripping members 35a and 35b, so that the endoscope E can be turned in a state in which the endoscope E is fixed at the predetermined insertion position.

In the endoscope holder 31, the first gripping member 35a and the second gripping member 35b are swingably held, in the lengthwise direction of the endoscope housing part 34, by the spring 44 disposed between the pressing member 43 and the first gripping member 35a, and by the springs 42 disposed between the inner bottom wall of the endoscope housing part 34 and the second gripping member 35b, respectively. Then, the endoscope E can swing in an axial direction of the endoscope E in a state in which the endoscope E is fixed at the predetermined insertion position in the body.

At this time, in the endoscope holder 31, the columnar members 36a and 36c are inserted into the oblong hole portion 40 provided in each of the first and second gripping members 35a and 35b, the columnar member 36b is inserted into the circular hole portion 49a provided in the bridging portion 49 of the oblong hole portion 40, but the oblong hole portion 40 has a gap around each of the columnar members 36a and 36c, and the circular hole portion 49a has a gap around the columnar member 36b. Accordingly, even when the first and second gripping members 35a and 35b swing, the columnar members 36a, 36b, and 36c can be prevented from interfering with the first and second gripping members 35a and 35b, resulting that the first and second gripping members 35a and 35b can smoothly swing.

As illustrated by way of examples in which the endoscope E is a lower portion (large intestine) endoscope in FIGS.

12A and 12B, the endoscope holder 1 of the first aspect or the endoscope holder 31 of the second aspect of the present embodiment comprises an arm 51 supporting the holder main body 3, 32. The arm 51 comprises a plurality of joints 52 to securely hold the holder main body 3, 32 supporting the endoscope E at an arbitrary position and posture, and is fixed, by an arm fixing unit 54, to a bed 53 on which a patient P is positioned in a lateral decubitus position.

Figure 13:
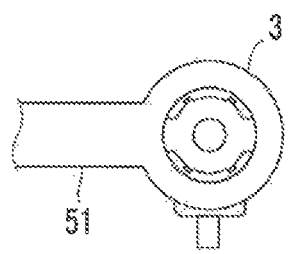
FIG. 13 is a diagram illustrating a distal end of the arm to which the holder main body of the endoscope holder illustrated in FIG. 1 is integrally fixed.
Figure 14A:
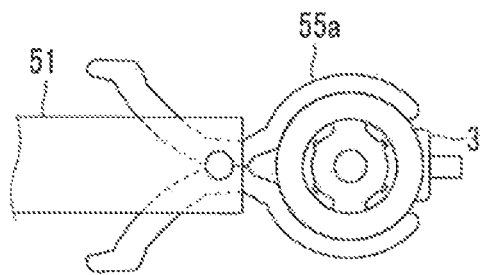
FIG. 14A is a front view illustrating a distal end of the arm to which the holder main body of the endoscope holder illustrated in FIG. 1 is detachably attached.
Figure 14B:
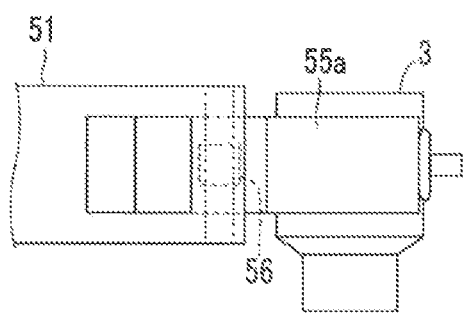
FIG. 14B is a bottom view of FIG. 14A.

Here, as illustrated in FIG. 13, the holder main body 3 of the endoscope holder 1 of the first aspect may be integrally fixed to a distal end of the arm 51, or as illustrated in FIGS. 14A and 14B, the holder main body 3 may be detachably attached to the distal end of the arm 51. As a unit configured to detachably attach the holder main body 3 to the distal end of the arm 51, for example, a clamp 55a which applies a clamping force using a torsional spring 56 can be used, as illustrated in FIGS. 14A and 14B.

Figure 15:
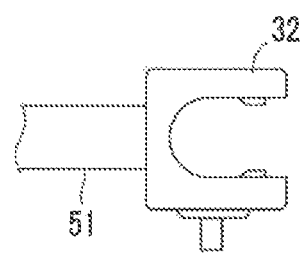
FIG. 15 is a side view illustrating a state in which the holder main body of the endoscope holder illustrated in FIG. 7 is integrally fixed to the distal end of the arm.
Figure 16A:
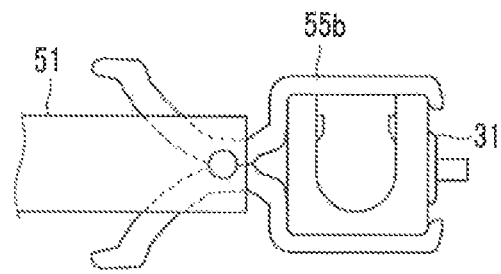
FIG. 16A is a front view illustrating a state in which the holder main body of the endoscope holder illustrated in FIG. 7 is detachably attached to the distal end of the arm.
Figure 16B:
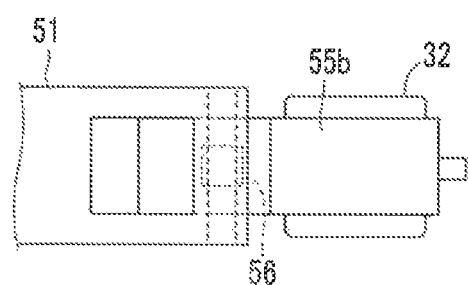
FIG. 16B is a side view of FIG. 16A.

As illustrated in FIG. 15, the holder main body 32 of the endoscope holder 31 of the second aspect may be integrally fixed to a distal end of the arm 51, or as illustrated in FIGS. 16A and 16B, the holder main body 32 may be detachably attached to the distal end of the arm 51. As a unit configured to detachably attach the holder main body 32 to the distal end of the arm 51, a clamp 55b which applies a clamping force using a torsional spring 56 can be used.

It is only required that the arm 51 can securely hold the holder main body 3 supporting the endoscope E at an arbitrary position and posture, and therefore various well-known arms can be used as the arm 51 itself.

Figure 17:
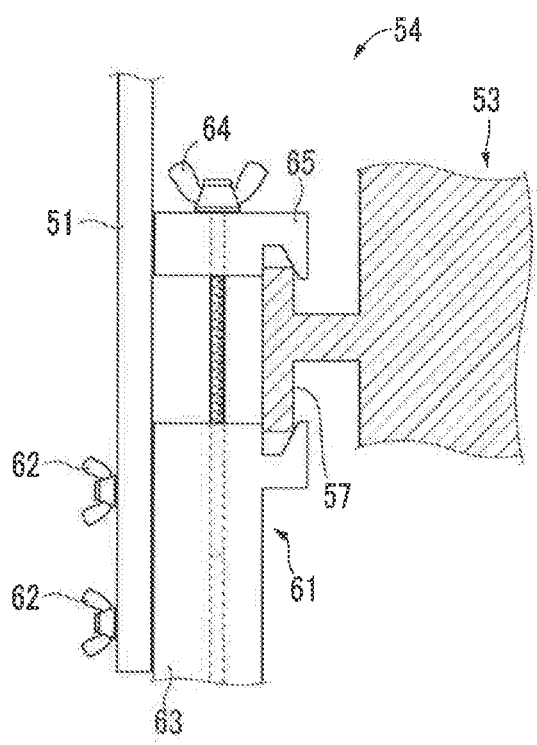
FIG. 17 is a diagram illustrating a method of fixing a proximal end of the arm illustrated in FIG. 12 to a bed with a rail by a clamp.
Figure 18:
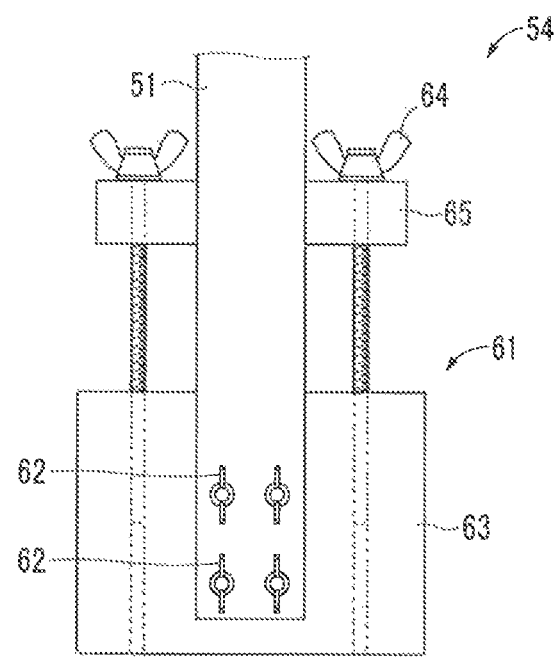
FIG. 18 is a front view of the clamp to which the proximal end of the arm illustrated in FIG. 17 is fixed.

As illustrated in FIG. 17 and FIG. 18, for example, as the arm fixing unit 54, a clamp 61 to configured to fix a proximal end of the arm 51 to a rail part 57 of the bed 53 can be used. The clamp 61 comprises a fixing part 63 which is screw-fitted to the proximal end of the arm 51 with thumbscrews 62, and a movable part 65 which is fastened toward the fixing part 63 with thumbscrews 64 which is screwed into the fixing part 63. The clamp 61 can be fixed to the rail part 57 by fastening the movable part 65 located on an upper side of the rail part 57 to the fixing part 63 which is brought into contact with a lower portion of the rail part 57 with the thumbscrews 64, and pinching the rail part 57 between the fixing part 63 and the movable part 65.

Figure 19:
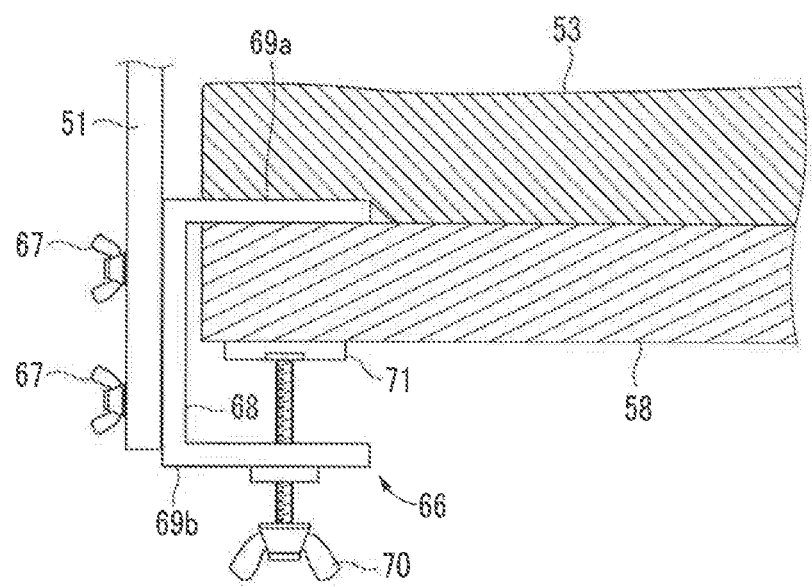
FIG. 19 is a diagram illustrating a method of fixing a proximal end of the arm illustrated in FIG. 10 to a bed frame by a clamp.
Figure 20:
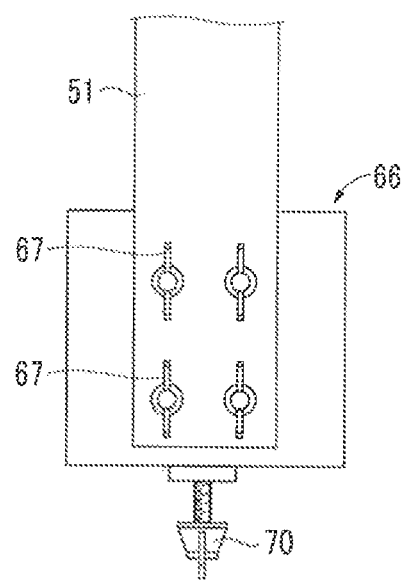
FIG. 20 is a front view of a C-shaped clamp to which the proximal end of the arm illustrated in FIG. 19 is fixed.

As illustrated in FIG. 19 and FIG. 20, as the arm fixing unit 54, a C-shaped clamp 66 to configured to fix a proximal end of the arm 51 to a frame 58 of the bed 53 can be used. The C-shaped clamp 66 comprises a fixing part 68 which is screw-fitted to the proximal end of the arm 51 with thumbscrews 67, claw portions 69a and 69b which protrude from both ends of the fixing part 68, respectively, in a direction perpendicular to the fixing part 68, and a washer part 71 which is fastened toward the claw portion 69a with a thumbscrew 70 which is screwed into the claw portion 69b. The C-shaped clamp 66 can be fixed to the frame 58 by fastening the washer part 71 toward the claw portion 69a which is brought into contact with an upper surface of the frame 58 with a thumbscrew 70 which is screwed into the claw portion 69b located below the frame 58, and pinching the frame 58 between the claw portion 69a and the washer part 71.

The arm fixing unit 54 is not limited to an arm fixing unit configured to fix the arm 51 to the rail part 57 or the frame 58 of the bed 53 as described above, but the arm fixing unit 54 may be fixed to another fixing member such as a table and a desk.

Note that a case where the lower portion (large intestine) endoscope is used as the endoscope E to be mounted to the holder main body 3, 32 supported by the arm 51 has been described in FIG. 12 to FIG. 20, but the endoscope holder 1, 31 of the present embodiment can be used by mounting an upper digestive tract endoscope as the endoscope E to the holder main body 3, 32.

REFERENCE SIGNS LIST 1, 31 Endoscope holder
2 Insertion hole
3, 32 Holder main body
6a, 6b, 36a, 36b, 36c Columnar member
7a, 35a First gripping member
7b, 35b Second gripping member
10, 39 Roller
11 Hole portion
12a, 12b, 41 Spring (first elastic member)
13, 43 Pressing member
14, 46 Spring (third elastic member)
15, 42 Spring (second elastic member)
17, 47 Lever (switching mechanism)
21 Deaeration preventing valve
22 Annular member
40 Oblong hole portion

The invention claimed is:

1. An endoscope holder which fixes and holds an endoscope inserted into a body at a predetermined insertion position, comprising:
   a holder main body having a hollow quadratic shape which comprises an endoscope housing part with an opening in one side surface thereof, the endoscope housing part being configured to house the endoscope therein;
   first and second gripping members each having a plate-like body extending in a lengthwise direction of the endoscope housing part, and contacts the endoscope housed in the endoscope housing part to pinch the endoscope;
   a first elastic member which is disposed between the first and second gripping members and urges the first and second gripping members in a direction in which the first and second gripping members are separated from each other;
   a pressing member which presses the first gripping member toward the second gripping member against an urging force of the first elastic member;
   a switching mechanism which holds or releases a pressing state by the pressing member;
   rollers which are rotatably provided at surfaces of the first and second gripping members which are in contact with the endoscope, along the lengthwise direction of the endoscope housing part; and
   a second elastic member which is provided between the second gripping member and an inner wall of the endoscope housing part, and swingably supports the second gripping member with respect to the lengthwise direction of the endoscope housing part.

2. The endoscope holder according to claim 1, wherein
A plurality of the second elastic members are disposed in at least two positions along the lengthwise direction of the endoscope housing part.

3. The endoscope holder according to claim 1, further comprising:
   a third elastic member which is disposed between the first gripping member and the pressing member and swingably supports the first gripping member with respect to the lengthwise direction of the endoscope housing part.

4. The endoscope holder according to claim 1, further comprising:
  a restricting member on an inner wall surface of the endoscope housing part,
  wherein the restricting member restricts mutual approach between the first and second gripping members.

5. The endoscope holder according to claim 1, further comprising:
  a plurality of columnar members erected along a side surface facing the opened side surface of the endoscope housing part,
  wherein the first and second gripping members comprise oblong hole portions into which the columnar members are to be inserted, and
  the oblong hole portions each have at least a gap in the lengthwise direction of the endoscope housing part with respect to the columnar member.

6. The endoscope holder according to claim 1, further comprising:
  an arm supporting the holder main body at an arbitrary position and posture,
  wherein the holder main body is integrally fixed to a distal end of the arm or detachably attached to the distal end.

7. The endoscope holder according to claim 6, further comprising:
  an arm fixing unit configured to detachably fix a proximal end of the arm to a frame or a rail part of a bed, or another fixing member.

8. The endoscope holder according to claim 1, wherein the endoscope is an upper digestive tract endoscope or a lower portion endoscope.

* * * * *